United States Patent [19]
Bean

[11] Patent Number: 5,720,930
[45] Date of Patent: Feb. 24, 1998

[54] CONTAINER FOR WASHER OR AUTOCLAVE

[76] Inventor: Douglas Colin Bean, 82 Lewis Road, Wantirna South, Victoria 3152, Australia

[21] Appl. No.: 751,931

[22] Filed: Nov. 12, 1996

Related U.S. Application Data

[63] Continuation-in-part of PCT/AU95/00282, May 12, 1995, published as WO95/31222, Nov. 23, 1995.

[51] Int. Cl.$^6$ .................... A61L 2/00; B65D 1/34; B65D 6/10
[52] U.S. Cl. .................... 422/300; 422/297; 220/572; 220/607; 206/370; 206/438; 428/167
[58] Field of Search .................. 428/167; 433/77; 206/557, 370, 367, 438, 439; 134/182, 201; 220/607, 571, 572; 422/297, 300

[56] References Cited

U.S. PATENT DOCUMENTS 4,157,145  6/1979  Jordan .................... 220/487

*Primary Examiner*—Robert J. Warden
*Assistant Examiner*—Alex Noguerola
*Attorney, Agent, or Firm*—Gilliam, Duncan Harms

[57] ABSTRACT

A container for enabling fluid flow therethrough for cleaning or sterilizing of the contents, comprises a tray (10) and lid (20) and having respective bases (11, 21) and side walls (17, 27). The bases (11, 21) have perforations (12, 22) defined by elliptically shaped perforation walls (13, 23) with their major axes vertical to allow easy flow of the cleaning fluid through the container and minimum contact points with the contents or other containers.

16 Claims, 4 Drawing Sheets

CONTAINER FOR WASHER OR AUTOCLAVE

This is a continuation-in-part of our international application PCT/AU95/00282, with an international filing date of May 12, 1995, which is now WO 95/31222 Nov. 23, 1995.

TECHNICAL FIELD

This invention relates to a container component for enabling fluid flow therethrough for cleaning or sterilizing of the contents within the container.

BACKGROUND ART

In medical and dental establishments, because of environmental problems and the cost and difficulty of burning and dumping of medical waste, there is a growing tendency to return to reusable products. For example medical and dental instruments after use are frequently returned in a container to a washing or sterilizing facility where the instruments are decontaminated. The instruments can then be safely handled without risk from infections such as HIV and Hepatitis caused by inadvertent cutting or puncturing of the person handling a contaminated instrument. The instrument can be cleaned and serviced as necessary and sterilization in an autoclave follows, usually with porous filter medium surrounding the tray or other container holding the instruments. The instruments while remaining protected by the porous wrapping are then stored and subsequently returned to the surgery for reuse by the dentist or doctor.

Trays made of stainless steel and synthetic materials are known for holding dental and medical instruments for sterilization in an autoclave. Such stainless steel trays have a base made of a sheet of flat stainless steel material which has an array of cylindrical holes drilled through the base to allow steam in the autoclave to pass through the base. However such stainless and synthetic steel trays are expensive and/or may not allow steam or washing liquid to reach all parts of the instruments resting on them.

Patent Specification No. AU-24539/88 discloses an autoclave container in the form of a tray made of a plastics material, the tray having a base with perforations defined by walls, the walls progressively widening from a top point to a flat bottom surface of the base. The flat bottom surface enables a substantial amount of the heat stored within the plastics material after the tray has been an autoclave to be yielded up through the flat base surface and thereby help evaporate any moisture, such as condensation, particularly within the filter material placed around the tray when in the autoclave. However the tray in this patent specification would not be particularly effective in a washer where water jets are directed upwardly against the base of the tray, since the large flat bottom surface area would deflect much of the water downwardly rather than allowing the water to pass upwardly through the perforations to reach the instruments in the tray.

A type of closed autoclave vessel frequently used in hospitals for holding instruments to be sterilised in an autoclave has a square bottom of about 40 cm width and which has a perforated central opening, e.g. having a diameter of about 10 cm. The circular central opening in use is covered by a permeable filter material. The lid of the vessel is similarly constructed, having a 10 cm diameter circular perforated opening in the centre of the lid covered in use by a permeable filter. Inside the closed vessel there can be a tray which is perforated and which supports the instruments to be sterilised. Steam flows through the upper circular opening in the lid to reach the interior of the vessel and passes out through the lower central perforated opening. The flow of steam through such a vessel tends to be greatest in the central region of the space enclosed within the vessel, this effect being the result of the steam flowing through a path of least resistance. Hence it is possible that the outer sides and particularly the corners of the vessel may be inadequately heated to effectively sterilize the instruments at the edges or in the corners of the vessel.

It is an object of the present invention to provide a container component for enabling fluid flow therethrough for improved efficiency or effectiveness of the cleaning of contents of the container in which the fluid can be in a liquid gaseous or plasma state.

It is a preferred object to provide a container component suitable for placement within a washer in which washing liquid is directed upwardly and/or downwardly so as to pass through the container component thereby washing articles in the container.

It is a further preferred object to provide a container component suitable for use in sterilization or cleaning processes using a cleaning fluid such as a gas sterilant or oxidizing gas, for example a peroxide gas enabling the cleaning fluid to effectively flow through the container component whether in a gaseous, liquid or plasma state at high temperatures or atmospheric temperatures.

It is a further preferred object of the present invention to provide a container component suitable for use in an autoclave and enabling steam to flow through the container component for effective sterilization of articles in the container.

It is a further preferred object to provide simple and effective means for supporting articles such as surgical instruments in a container for cleaning or sterilizing.

SUMMARY OF INVENTION

According to one aspect of the invention there is provided a container component for enabling cleaning of articles located within the container component by fluid flow through the component, and comprising a base, the base having perforations provided over substantially the entire area where the articles are in use located and through which the cleaning fluid can flow, the perforations in the base being defined by perforation walls, each of the walls in vertical cross section having a narrow top, widening in a downwards direction to a maximum width and then narrowing again to a narrow bottom, the maximum width being less than the distance from the top to the bottom.

According to another aspect of the invention them is provided a container for enabling cleaning of articles located within the container by fluid flow through the container, and comprising:

a tray, the tray having a bottom with perforations provided over substantially the entire area of the bottom where the articles are in use located and through which the cleaning fluid can flow;

a cover enabling covering of the articles in the container and having perforations over substantially its entire area and through which the cleaning fluid can flow;

wherein the perforations in the cover are defined by perforation walls, each of the walls of the cover having in vertical cross section a narrow top, widening in a downwards direction to a maximum width and then narrowing again to a narrow bottom, the maximum width being less than the distance from the top to the bottom; and wherein the perforations in the bottom of the tray are defined by perforation walls, each of the walls of the bottom having in vertical cross section a narrow top, widening in a downwards direction to a maximum width and then narrowing again to a narrow bottom, the maximum width of the wall of the bottom being less than the distance from the top to the bottom of that wall.

In the preferred embodiments, the narrow top of each perforation wall comprises a top point, and the narrow bottom of each perforation wall comprises a bottom point. The provision of walls which in section narrow in an upwards direction to a top point and in a downwards direction to a bottom point provides for minimum area of contact with other bodies. For example, in the case of a tray or bottom section of a vessel constructed according to the invention having articles to be cleaned placed in the tray resting on the base, the articles will contact the base only at the top points of the walls so that the maximum surface areas of the articles are exposed for contact by the cleaning fluid. The external bottom surface of a tray will present the bottom points of the perforation walls as contact points so that if, for example, a tray is stacked immediately on top of another container having a lid constructed according to the invention, the contact points will be the bottom points of the walls of the tray and the top points of the walls of the lid, thus minimising contact area where moisture may collect.

The base may be substantially planar and each wall in vertical cross section may be substantially elliptical with the major axis of the elliptical cross section being orthogonal to the plane of the base.

Alternatively, each wall in vertical cross section may widen gently and progressively in a downwards direction from the narrow top to the maximum width and then may narrow rapidly and sharply to the narrow bottom, or vice versa.

By providing that the maximum width of each wall is less than the distance from the top point to the bottom point, the proportion of the total area of the base in plan view occupied by the area of the perforations, and hence the area open to flow of cleaning fluid through the base can be maximised while at the same time the walls can provide sufficient structural strength. The maximum width of each wall may be, for example, less than half the distance from the top to the bottom thereof.

The walls may define a regular geometric mesh pattern. For example, with walls arranged in a square mesh pattern, the walls having a maximum width of 2 mm and the spacing between opposite walls of each square perforation being 3.5 mm, about 40% of the area of the base will in plan view be defined by the sum of the areas of the perforations. The cumulative area of the perforations when the base is viewed in plan view may be greater than 30%, e.g. equal to or greater than 40%, of the total area of the base.

The container component according to the first aspect of the invention may comprise a tray, the base of the component defining a bottom of the tray, a plurality of side portions located around the perimeter of the base, the perforations in the base being provided over substantially the entire surface area out to the perimeter where the side portions are located, so that the articles to be cleaned are located by the side portions entirely within the perimeter of the base where the perforations are provided, the tray having an open top through which the cleaning fluid can flow.

The container component may include a plurality of article supports projecting up above the base to support articles to be cleaned, each of the article supports comprising an upright projection mounted to the base by a resilient formation which fits and is retained within a respective perforation. The upright projection of each of the article supports in one embodiment comprises an elongated web having a top edge which is narrow in cross section so that the articles to be cleaned rest on the top edge with essentially a point contact, the resilient formation being an elongated resilient formation and the perforation in the base which receives the resilient formation being similarly an elongated perforation. In an alternative embodiment, the resilient formation of each of the article supports comprises a resilient plug which fits in an associated perforation in the base, the upright projection comprising a post having a formation at its upper end for directly supporting an article to be cleaned or for mounting of other members which in turn support an article to be cleaned.

The container in use may have an outside wrap such as a filter membrane around the outside, or may have a filter membrane held within the container so that cleaning fluid passes through the filter membrane in flowing to or flowing from the articles.

The container component may be, as mentioned above, in the form of an open-topped tray for containing articles to be cleaned. Alternatively, there may be provided a container or cassette comprising a bottom section of a two part enclosure, such as an autoclave vessel having a bottom section in which the articles are located and a cover or lid section which fits to and is secured to the bottom section. Either or both the bottom section and the lid section of the two part vessel may be constructed according to the present invention.

In the case of a container component to be placed in a washer in which streams of washing liquid are directed so as to contact and wash articles within the container component, the construction of the walls according to the invention facilitates washing liquid which is directed against the base being deflected or directed so as to pass through the perforations into the space where the articles to be cleaned are located.

The container component may be made of a plastics material, particularly in the case of use in sterilizing operations being a material capable of withstanding autoclave temperatures. A preferred material is polypropylene.

BRIEF DESCRIPTION OF DRAWINGS

Possible and preferred features of the present invention will now be described with particular reference to the accompanying drawings. However it is to be understood that the features illustrated in and described with reference to the drawings are not to be construed as limiting on the scope of the invention. In the drawings.

DETAILED DESCRIPTION

Figure 1:
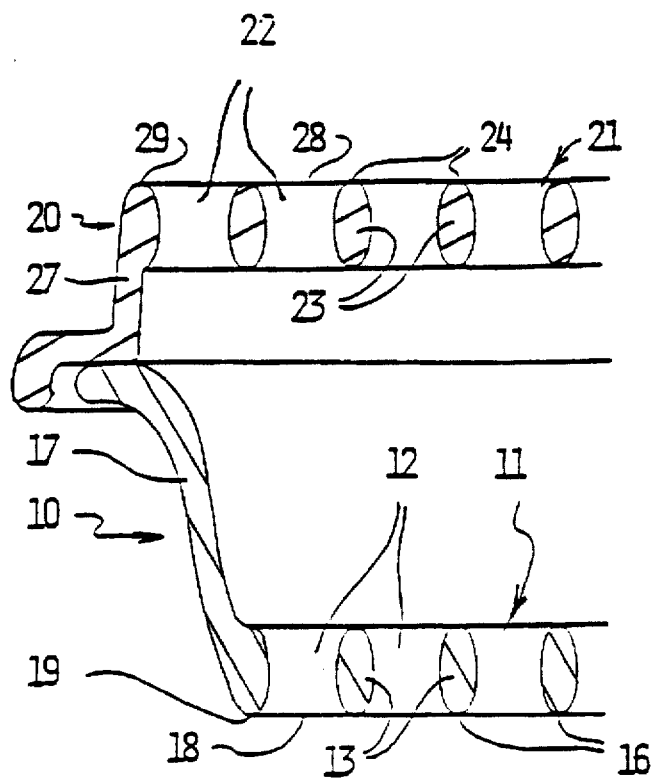
FIG. 1 shows a cross-section through a fragment of a container having a tray and a lid both embodying the present invention.
Figure 2:
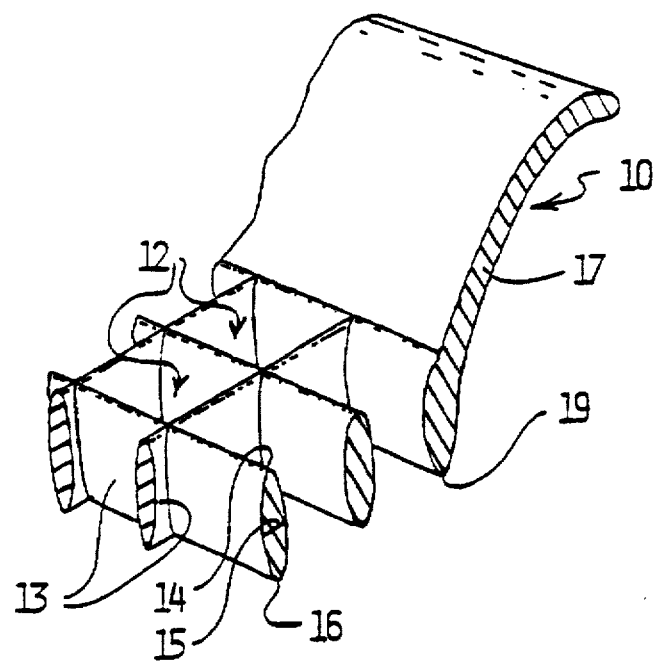
FIG. 2 shows a fragmentary perspective sectional view of a portion of a container component according to the invention.

The two part container shown in FIGS. 1 and 2 comprises a tray 10 and a cover or lid 20 each of which embodies the present invention. However the invention also relates to simple open topped trays such as the tray 10, e.g. for holding dental instruments to be placed in a washing apparatus where washing water containing disinfectant is directed in multiple directions within the washer so as to pass through the tray and wash the articles in the tray.

The tray 10 includes a base 11. Similarly the lid 20 has a base 21. The base 11 has perforations 12 and similarly the lid 20 has perforations 22 to allow cleaning fluid, such as water in a washer or steam in an autoclave, to pass through the base 11 or 21 to contact articles received within the tray 10.

The tray 10 and lid 20 can be moulded from plastics material such as polypropylene capable of withstanding autoclave temperatures.

The tray 10 has a side wall 17 extending upwardly from the perimeter or edge of the perforated base 11, and the lid 20 has side wall 27 having a complementary shape at its edge to the top of the side wall 17 to enable the lid 20 to fit to the tray 10.

As shown in FIG. 2, the perforations 12 are defined by perforation walls 13. Each wall 13 in vertical cross-section is elliptical with the major axis vertical so as to commence at a top point 14, widen in a downwards direction to a maximum width 15 corresponding to the minor axis of the ellipse, and then narrow to a bottom point 16. The maximum width 15 is less than the distance from the top point 14 to the bottom point 16, i.e. the major axis. In FIGS. 1 and 2, the width 15 is less than half the distance from point 14 to point 16.

With this shape of the walls 13, the cumulative area of the perforations 12 in plan view can be maximised for flow of water or steam through the perforations. The narrowing of the shape from the width 15 downwardly to the bottom point 16 enables much of the water directed upwardly in a washer against the tray 10 to be deflected into the perforations 12 so that most of the water being directed upwardly can continue to flow upwardly through the perforations 12 to reach articles within the tray 10 even if the water first impinges on the walls 13.

The particular shape of the walls with the widening in a downwards direction from the top point 14 also facilitates effective cleaning of articles within the tray. In particular, articles placed within the tray 10 will rest on the base 11 with essentially points of contact where the articles touch the top points 14 whereby washing fluid or steam passing through the base can reach substantially the entire surface areas of the articles.

As seen in FIG. 1, the bottom points 16 of the tray 10 define a bottom plane 18 and the bottom edge 19 of the wall 17 meets but does not extend below this plane 18. Also, the walls 13 and perforations 12 are provided across the entire area of the base 11 so that the bottom edge 19 of the side wall 17 presents only the same area in bottom plan view as a perforation wall 13. This enables articles in the tray 10, even if they are located at one side against a side wall 17, to be reached and contacted by cleaning fluid passing upwardly or downwardly through the container.

Figures 3A, 3B, 3C, 3D, 3E:
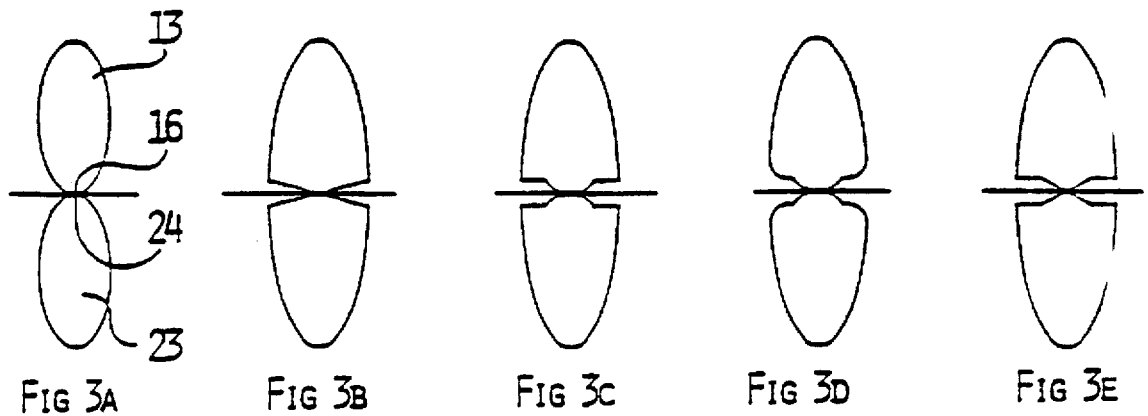
FIGS. 3a to 3e show possible cross-sectional shapes of walls and how they would contact similar shaped walls of another base.

The same functional features are provided by the lid 20 so that the top points 24 of the walls 23 define a plane 28 and the side wall 27 at its top edge 29 does not project above this plane 28. This construction enables containers comprising tray 10 and lid 20 as shown in FIG. 1 to be stacked one on top of each other with contact points being restricted to the bottom points 16 of tray 10 meeting and resting on top points 24 of a lid 20. This minimises the contact surface areas between stacked containers to minimise obstruction to flow of cleaning fluid through the stacked containers and also to minimise areas where moisture could collect at the areas of contact. FIG. 3a shows the point contact provided by the bottom point 16 of wall 13 meeting the top point 24 of wall 23.

FIGS. 3b to 3e show alternative cross-sectional shapes for walls 13, 23 which still satisfy the parameters of the present invention and enable point contact of abutting container component bases.

Figure 4:
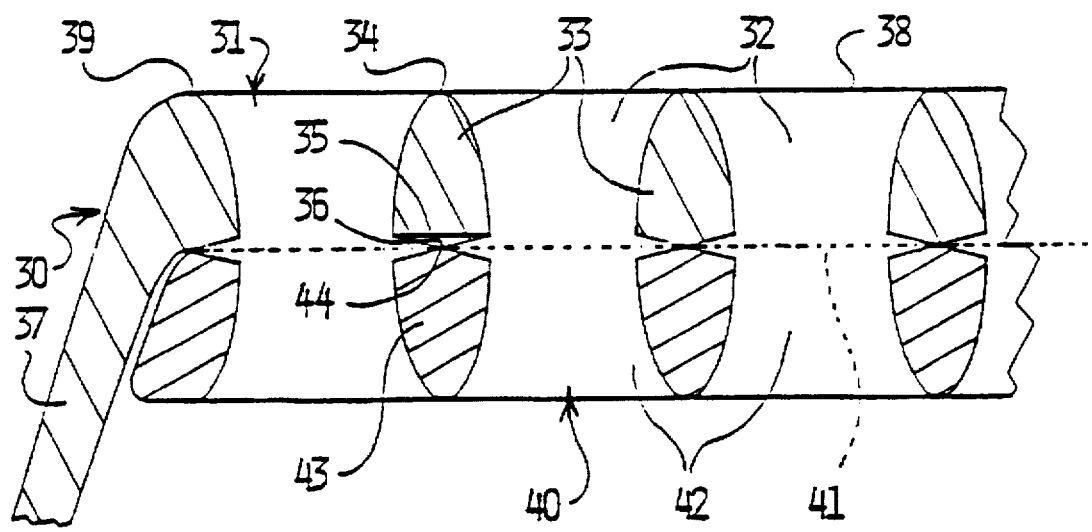
FIG. 4 shows a fragmentary cross-sectional view of a component of a stackable autoclave container embodying the present invention and holding a filtering membrane.

FIG. 4 shows a fragmentary cross-section of the lid of an enclosed autoclave basket or vessel, the lid 30 having a base 31 provided with perforations 32 through which steam can flow into the vessel. The walls 33 have the shape shown in FIG. 3b and satisfy the parameters of the present invention. In particular, the walls 33 in cross-section start at a narrow top point 34, widen downwardly to a maximum width 35 and then narrow to a bottom point 36. In this case, the cross-section rapidly narrows from the maximum width 35 to the bottom point 36 while the widening from the top point 34 to the maximum width 35 is shown as a half ellipse. The perforations 32 and walls 33 extend completely to the edge of the base 31 where the side wall 37 joins with the base 31 without the top edge 39 of the wall 37 projecting beyond the plane 38 defined by the top points 34.

Within the lid 30 there is provided a perforated filter retainer 40 which is used to clamp a filtering membrane 41 such as a polypropylene fibre gauze between the filter retainer 40 and the base 31. The filter retainer 40 can be clamped or retained within the lid 30 by any convenient attaching or clamping means (not shown). The filter retainer is constructed as a mirror image of the base 31 so that the filtering membrane 41 is clamped between the bottom points 36 of the base 31 and complementary co-operating top points 44 provided by the walls 43 of the retainer 40. This minimises the area of contact between the filtering membrane 41 and the base 31 and between the filtering membrane 41 and the filter retainer 40 so that steam passing through the perforations 32 in the base 31 and the perforations 42 in the filter retainer 40 can reach substantially the entire area of the filtering membrane 41. The essentially point contact between the points 36 and 44 minimises the risk of moisture condensation and retention at these contact points.

Figure 5:
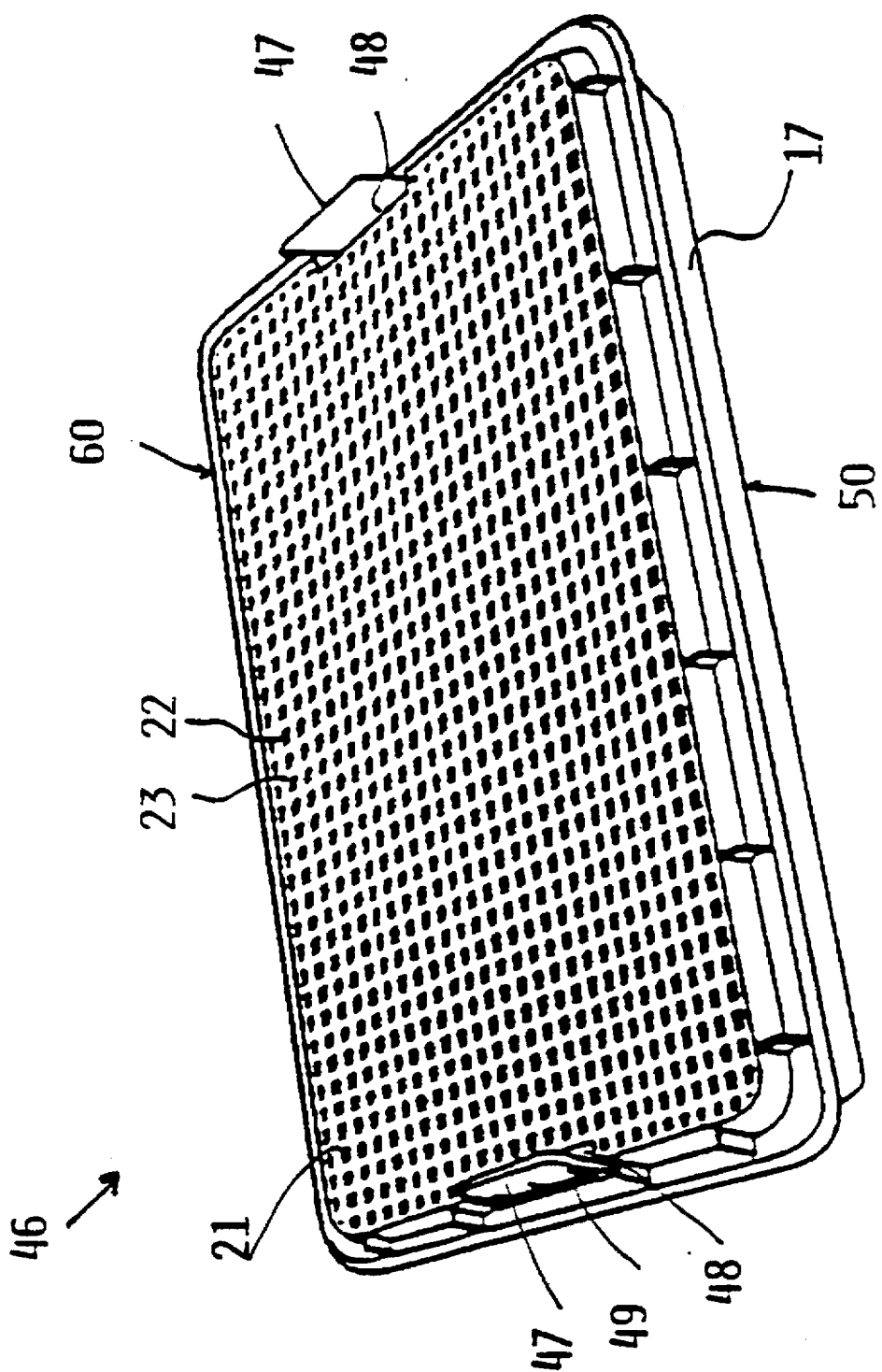
FIG. 5 shows a perspective view of a cassette having a tray and a lid according to the invention.

A tray forming the bottom of the autoclave container (of which FIG. 4 shows the lid assembly 30, 40, 41) can be substantially a mirror image of the lid construction shown in FIG. 4 so that the entire autoclave container can have a large area of perforations in the tray and also in the lid through which steam can flow. As shown in FIG. 5, the tray 50 and lid 60 can form a closeable cassette 46. Although the cassette 46 is formed from a tray 50 and a lid 60 which are not mirror images, the general structure is similar to the structure of the tray 10 and lid 20 shown in FIG. 1. The tray 50 and the lid 60 are rectangular and each includes a base 11, 21 having perforations 12, 22 to allow cleaning fluid, such as water or steam, to enter into the cassette 46, contact the articles therein and exit the cassette. The perforations in the tray 50 of cassette 46 of FIG. 5 can be defined by perforation walls as shown in FIG. 2. Similarly the lid 60 has perforations 22 defined by perforation walls 23. Each wall 13, 23 in vertical cross-section is elliptical with the major axis vertical so as to commence at a top point, widen in a downwards direction to a maximum width corresponding to the minor axis of the ellipse, and then narrow to a bottom point. The maximum width is less than the distance from the top point to the bottom point.

At each central position of the shorter opposite ends of the lid 60 is a slot 48 extending parallel to the end edges of the tray 50. The tray 50 has at each corresponding position in each shorter opposite side 17 a tongue 47 formed integral with the side walls 17 and extending above the top perimeter of the side walls 17. Each tongue is inserted through the corresponding slot 48 of the lid 60 when the lid 60 is placed on the tray 50 in a closed position. The tongues 47 extend up from close to the base of the tray so as to provide a useable degree of resilience. This resilience is used to close the cassette 46 by the resilient tongue 47 being able to be moved inwardly from its resting position while being inserted through the corresponding slot 48 and, upon release, engage the respective outer side of the slot 48 while trying to return to its resting position. Each tongue 47 includes a step 49 extending across its outer side to engage the end of the lid 60 so as to releasably lock the lid 60 onto the tray 50.

It can be seen that with the constructions of FIGS. 4 or 5, similarly constructed autoclave containers can be stacked on top of each other within the autoclave with minimised obstruction to flow of steam through the successive stacked containers. In particular, the top points 34 of the lid 30 will form point contacts only with complementary bottom points of the walls provided in the tray of the superimposed container.

Figure 6:
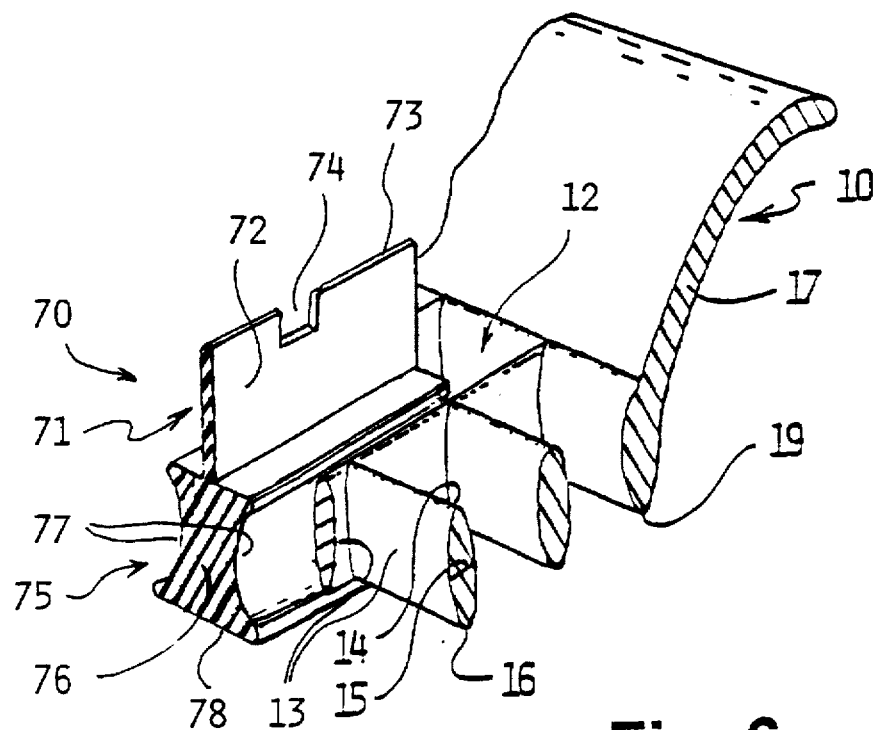
FIG. 6 shows a portion of a container similar to FIG. 2 and provided with an article support.
Figure 7:
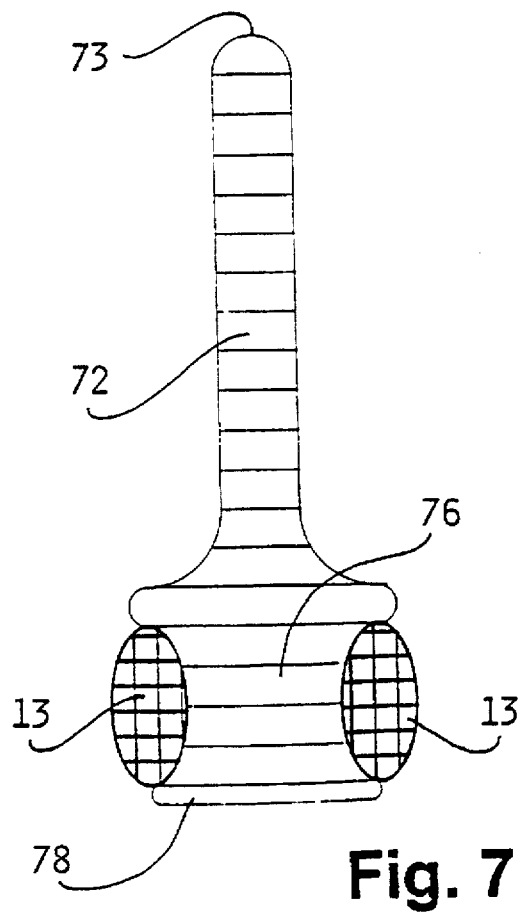
FIG. 7 shows a cross sectional view through the article support of FIG. 6 in use.
Figure 8:
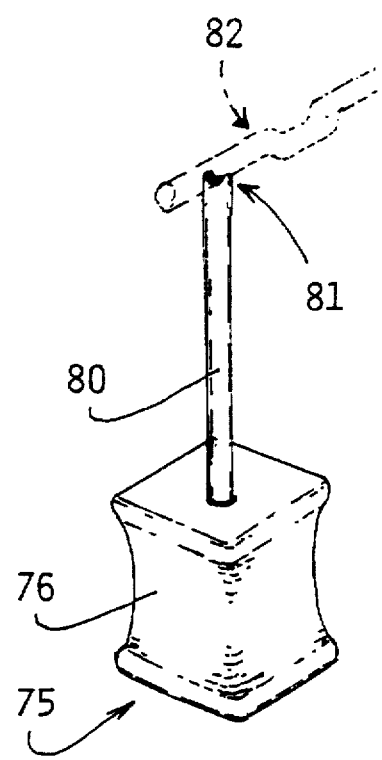
FIG. 8 shows an alternative configuration of an article support.

To support articles, particularly delicate and/or expensive articles such as surgical instruments, endoscopic apparatus and the like, there may be provided article supports 70 projecting up above the base 11. As shown in FIG. 6, 7, and 8 each article support can take the form of an upright projection 71 mounted to the base by a resilient formation 75 which fits and is retained within a respective perforation.

In FIGS. 6 and 7, the article support 70 has an upright projection 71 in the form of an elongated web 72 having a top edge 73 which is narrow in cross section so that articles rest on the top edge 73 with essentially a point contact. There may be concavities such as notches 74 at spaced locations in the top edge to more positively locate and retain articles such as delicate or expensive medical instruments. The perforation 12 in the base receiving and mounting the article support 70 is an elongated perforation rather than a relatively small square perforation as the others are. As best shown in the cross sectional view in FIG. 7, the resilient formation 75 is in the form of a plug 76 of resilient material such as silicone which has a complementary shape to the cross sectional shape of the perforation in which it fits.

In particular, the plug 76 has concavities 77 which are of complementary shape to the profile of the walls 13 defining the perforation so that the plug is a tight fit and does not leave cavities where moisture can condense or collect leading to contamination risks. The plug is preferably of slightly larger dimensions than the perforation to utilise the resilience of the material to form the right sealing fit without cavities that might harbour moisture. The bottom 78 of the plug 76 is illustrated as projecting slightly below the plane 18 defined by the bottom points 16 so that the bottom 78 constitutes a foot on which the tray rests when placed on a support surface such as a bench top. The preferred resilient silicone material of the plug 76 means that the foot resists sliding or skidding of the tray on the support surface.

In FIG. 8, the article support 70 is in the form of a resilient plug 76 which fits in an associated perforation, the plug 76 mounting an upright projection 71 in the form era post 80 which can have any desired formation 81 at its upper end, e.g. for directly supporting an article to be cleared or for mounting of other members 82 such as beams or rails extending between a number of similar article supports 70. With this system, a user can configure any suitable arrangement of supports for the particular article to be cleaned such as a medical instrument of unusual shape.

In the embodiment of FIGS. 6 to 8, the article support 70 may be more securely or permanently anchored in place by a screw (not shown) inserted upwardly into the plug 76 to wedge the plug between the walls 13.

It will be seen that the container component, whether it be a tray or lid or cassette, according to the present invention enables articles to be effectively reached by cleaning fluid, such as washing liquid in a washer or steam in an autoclave. The cleaning fluid can also be a peroxide gas or any other gas sterilant or oxidizing gas. Also the cleaning fluid may be in liquid, gaseous or plasma state. Apart from use in high temperature or pressure sterilizing operations such as an autoclave the container component may be used in microwave sterilization processes.

I claim:

1. A container component for enabling cleaning of articles located within the container component by fluid flow through the component, and comprising a base, the base having perforations provided over substantially the entire area where the articles are in use located and through which the cleaning fluid can flow, the perforations in the base being defined by perforation walls each of the walls in vertical cross section having a narrow top, widening in a downwards direction to a maximum width and then narrowing again to a narrow bottom, the maximum width being less than the distance from the top to the bottom.

2. A container component as defined in claim 1 wherein the narrow top of each perforation wall comprises a top point, and the narrow bottom of each perforation wall comprises a bottom point.

3. A container component as defined in claim 2 wherein the base is substantially planar and wherein each wall in vertical cross section is substantially elliptical with the major axis of the elliptical cross section being orthogonal to the plane of the base.

4. A container component as defined in claim 2 wherein each wall in vertical cross section widens gently and progressively in a downwards direction from the narrow top to the maximum width and then narrows rapidly and sharply to the narrow bottom, or vice versa.

5. A container component as defined in claim 1 wherein the maximum width of each wall is less than half the distance from the top to the bottom thereof.

6. A container component as defined in claim 1 wherein the cumulative area of the perforations when the base is viewed in plan view is greater than 30% of the total area of the base.

7. A container component as defined in claim 6 wherein the cumulative area of the perforations when the base is viewed in plan view is equal to or greater than 40% of the total area of the base.

8. A container component as defined in claim 1 wherein the component comprises a tray, the base of the component defining a bottom of the tray, a plurality of side portions located around the perimeter of the base, the perforations in the base being provided over substantially the entire surface area out to the perimeter where the side portions are located, so that the articles to be cleaned are located by the side portions entirely within the perimeter of the base where the perforations are provided, the tray having an open top through which the cleaning fluid can flow.

9. A container component as defined in claim 1 and further including a plurality of article supports projecting up above the base to support articles to be cleaned, each of the article supports comprising an upright projection mounted to the base by a resilient formation which fits and is retained within a respective perforation.

10. A container component as defined in claim 9 wherein the upright projection of each of the article supports comprises an elongated web having a top edge which is narrow in cross section so that the articles to be cleaned rest on the top edge with essentially a point contact, the resilient formation being an elongated resilient formation and the perforation in the base which receives the resilient formation being similarly an elongated perforation.

11. A container component as defined in claim 9 wherein the resilient formation of each of the article supports comprises a resilient plug which fits in an associated perforation in the base, the upright projection comprising a post having a formation at its upper end for directly supporting an article to be cleaned or for mounting of other members which in turn support an article to be cleaned.

12. A container comprising a tray and a cover defining therebetween a space in which articles to be cleaned can be located, the tray comprising a container component as defined in claim 1 and the cover comprising a container component as defined in claim 1.

13. A container for enabling cleaning of articles located within the container by fluid flow through the container, and comprising:

a tray, the tray having a bottom with perforations provided over substantially the entire area of the bottom where the articles are in use located and through which the cleaning fluid can flow;

a cover enabling covering of the articles in the container and having perforations over substantially its entire area and through which the cleaning fluid can flow;

wherein the perforations in the cover are defined by perforation walls, each of the walls of the cover having in vertical cross section a narrow top, widening in a downwards direction to a maximum width and then narrowing again to a narrow bottom, the maximum width being less than the distance from the top to the bottom; and wherein the perforations in the bottom of the tray are defined by perforation walls, each of the walls of the bottom having in vertical cross section a narrow top, widening in a downwards direction to a maximum width and then narrowing again to a narrow bottom, the maximum width of the wall of the bottom being less than the distance from the top to the bottom of that wall.

14. A container as defined in claim 13 wherein the narrow top of each perforation wall comprises a top point, and the narrow bottom of each perforation wall comprises a bottom point.

15. A container as defined in claim 13 wherein the base is substantially planar and wherein each wall in vertical cross section is substantially elliptical with the major axis of the elliptical cross section being orthogonal to the plane of the base.

16. A container as defined in any one of claims 13 wherein there is provided a perforated filter retainer which clamps a filtering membrane between the filter retainer and the base, the filter retainer being constructed as a mirror image of the base so that the filtering membrane is clamped between the bottom points of the base and complementary co-operating top points provided by the retainer, whereby the area of contact between the filtering membrane and the base and between the filtering membrane and the filter retainer is minimised so that cleaning fluid passing through the perforations in the base and the perforations in the filter retainer can reach substantially the entire area of the filtering membrane.

* * * * *